US012796630B2

(12) United States Patent
Du et al.

(10) Patent No.: US 12,796,630 B2
(45) Date of Patent: Nov. 17, 2026

(54) METHOD FOR HIGH-EFFICIENCY REGENERATION OF POTATO PROTOPLAST

(71) Applicants: INNER MONGOLIA UNIVERSITY, Hohhot (CN); Inner Mongolia Open University, Hohhot (CN)

(72) Inventors: Miru Du, Hohhot (CN); Jianjian Qi, Hohhot (CN); Guochao Xuanyuan, Hohhot (CN); Yumeng Hu, Hohhot (CN); Xiao Li, Hohhot (CN); Yuanyuan Pu, Hohhot (CN); Zhiwen Feng, Hohhot (CN)

(73) Assignees: INNER MONGOLIA UNIVERSITY, Hohhot (CN); Inner Mongolia Open University, Hohhot (CN)

( * ) Notice: Subject to any disclaimer, the term of this patent is extended or adjusted under 35 U.S.C. 154(b) by 0 days.

(21) Appl. No.: 19/339,434

(22) Filed: Sep. 25, 2025

(65) Prior Publication Data

US 2026/0107894 A1 Apr. 23, 2026

(30) Foreign Application Priority Data

Oct. 10, 2024 (CN) ......................... 202411408500.9

(51) Int. Cl.
*A01H 4/00* (2006.01)

(52) U.S. Cl.
CPC .................................... *A01H 4/008* (2013.01)

(58) Field of Classification Search
CPC ......... A01H 4/008; A01H 4/005; A01H 4/002
See application file for complete search history.

(56) References Cited

PUBLICATIONS

None.*

Xiao Li, Regeneration of Potato Protoplasts and Transient Transformation Using CRISPR/ CAS9, Inner Mongolia University, 2019, pp. 1-54.

Xingkui Cai, Creation and genetic analysis of new germplasms resistant to Ralstonia solanacearum via cell fusion in potatoes, Huazhong Agricultural University, 2003, pp. 1-141.

* cited by examiner

*Primary Examiner* — Susan McCormick Ewoldt

(74) *Attorney, Agent, or Firm* — Bayramoglu Law Offices LLC

(57) ABSTRACT

A method for high-efficiency regeneration of a potato protoplast is provided, including the following steps: S1, conducting test-tube seedling cultivation; S2, conducting protoplast preparation; S3, conducting callus proliferation; S4, conducting callus synchronization; and S5, conducting callus induction regeneration. Protoplasts derived from treated potato leaves are induced to form a callus. Through callus synchronization and callus induction regeneration, high-efficiency and synchronized budding is achieved, significantly shortening the regeneration timeline of protoplasts and markedly enhancing the bud regeneration rate. This method provides abundant experimental materials for potato genetic improvement and cultivar development, and ensures consistency and stability of regenerated plantlets. This method also offers technical support for downstream applications, including: genetic theory research, high-throughput virus-free plantlet regeneration, and gene-editing breeding in potatoes.

2 Claims, 9 Drawing Sheets

METHOD FOR HIGH-EFFICIENCY REGENERATION OF POTATO PROTOPLAST

CROSS-REFERENCE TO THE RELATED APPLICATIONS

This application is based upon and claims priority to Chinese Patent Application No. 202411408500.9, filed on Oct. 10, 2024, the entire contents of which are incorporated herein by reference.

TECHNICAL FIELD

The present disclosure belongs to the technical field of potato cultivation, and in particular relates to a method for high-efficiency regeneration of potato protoplast.

BACKGROUND

Plant protoplast regeneration involves removing cell walls from plant cells to form protoplasts, which are then regenerated into whole plants under specific culture conditions. Potato stands as one of the earliest crops successfully subjected to in vitro culture for somatic hybrid plant regeneration. Protoplast culture and regeneration serve as pivotal steps in somatic hybridization, a technique that overcomes limitations in conventional potato breeding caused by ploidy levels and the endosperm balance number (EBN). Existing technologies primarily focus on preparing viable potato protoplasts, with achievements concentrated in the protoplast preparation stage. Leveraging the cell-wall-free nature of protoplasts, these methods facilitate transient genetic transformation and somatic hybridization studies. While leaves are the predominant source material, protoplasts are occasionally derived from stems, pollen, or hypocotyls for subsequent genetic transformation.

Current potato leaf protoplast regeneration systems suffer from two critical flaws: (1) asynchronous regeneration, leading to highly variable shoot bud emergence timelines within the same protoplast batch and developmental stage disparities; and (2) low regeneration rates, where the highest reported bud regeneration rate for potato leaf protoplasts is 22.9%. Most studies lack batch-specific regeneration rate analyses. Thus, there remains an urgent need to develop a technology that enhances both synchronization and regeneration rates of potato protoplasts.

SUMMARY

An objective of the present disclosure is to provide a method for high-efficiency regeneration of potato protoplast, with a short cycle and a high regeneration rate in view of the deficiencies in the prior art.

The objective of the present disclosure is achieved through the following technical solutions:

The present disclosure provides a method for high-efficiency regeneration of a potato protoplast, including the following steps:

step (1), conducting test-tube seedling cultivation;

step (2), conducting protoplast preparation;

step (3), conducting callus proliferation;

step (4), conducting callus synchronization: selecting callus with a diameter of 100 μm to 1,000 μm (having a relatively synchronous metabolic synthesis level and strong regeneration ability) from callus obtained in step (3), transferring the callus to a callus proliferation medium, adding a synchronization proliferation medium to allow cultivation at 4° C. to 7° C. for 1 day to 3 days to increase the synchronization level, and then conducting cultivation for 25 days in a cycle under light conditions at 20° C. to 23° C. for 16 hours and in the dark at 18° C. to 20° C. for 8 hours to form a green callus; where the callus proliferation medium is a solid medium, while the synchronization proliferation medium is a liquid medium; the solid-liquid bilayer culture system offers the following advantages: nutrients from the callus proliferation medium promote callus differentiation into plantlets; addition of the liquid synchronization proliferation medium without replacing the original medium prevents excessive division and proliferation of cells and callus; this enables synchronized regeneration, thereby further shortening the cultivation period; and step (5), conducting callus induction regeneration: transferring the green callus obtained in step (4) to a regeneration medium to allow cultivation for 40 days in a cycle under light conditions at 20° C. to 23° C. for 16 hours and in the dark at 18° C. to 20° C. for 8 hours to regenerate buds.

Further, the synchronization proliferation medium has a pH value of 5.6 to 6.0, and includes the following components: 4.33 g/L of Murashige and Skoog (MS) basal medium, 2 mg/L of glycine, 150 mg/L of myo-inositol, 0.5 mg/L of thiamine hydrochloride (vitamin B1), 0.5 mg/L of pyridoxine (vitamin B6), 5 mg/L of nicotinic acid, 0.5 mg/L of folic acid, 0.05 mg/L of biotin, 30 g/L of sucrose, 3 g/L of mannitol, 40 mg/L of adenine sulfate, 1 mg/L of naphthaleneacetic acid (NAA), 0.4 mg/L to 1.0 mg/L of 6-benzylaminopurine, 0.5 mg/L of indole-3-acetic acid (IAA), 0 mg/L to 5 mg/L of abscisic acid (ABA), and sterile water as a solvent.

Further, the bud regeneration medium has a pH value of 5.6 to 6.0, and includes the following components: 4.4 g/L of MS medium, 10 g/L of sucrose, 1 mg/L of zeatin or t-zeatin, 0.01 mg/L of NAA, 0 mg/L to 0.1 mg/L of gibberellic acid ($GA_3$), 6 g/L of agar, and sterile water as a solvent.

Further, step (1) specifically includes: subjecting a potato test-tube seedling to cultivation for 3 to 4 weeks in cycles under light conditions at 20° C. to 23° C. for 16 hours and in the dark at 18° C. to 20° C. for 8 hours.

Further, step (2) specifically includes:

step (a) conducting pre-cultivation: taking 2 to 3 fully expanded leaves on the upper part of a potato test-tube seedling cultivated in step (1) under sterile conditions, placing the leaves into pre-treatment medium I to allow cultivation in the dark at 24° C. for 1 day to 5 days, removing the pre-treatment medium I, and then transferring the leaves cultivated in the pre-treatment medium I into pre-treatment medium II to allow incubation in a refrigerator at 4° C. for 24 hours; where the pre-treatment medium II includes components such as myo-inositol and MES, wherein myo-inositol acts as an osmotic regulator, thereby maintaining osmotic balance between intra- and extracellular environments, while MES serves as a buffering agent to regulate and stabilize the solution's pH value; the pre-cultivation establishes a foundation for efficient and stable protoplast preparation, facilitating subsequent thorough enzymatic digestion to release protoplast cells from leaf tissues; low-temperature incubation preserves intracellular enzyme activity, slows cellular metabolic rates, and maintains structural integrity of the cells;

step (b) conducting enzymatic digestion: cutting pre-cultivated leaves obtained from step (a) into thin strips, immersing the thin strips in an enzymatic digestion solution to allow incubation in the dark at 28° C. for 9 hours to 10 hours, filtering an obtained enzymatic hydrolysate, centrifuging an obtained filtrate, and then discarding an obtained supernatant; and step (c) conducting protoplast purification: adding a Medium for Resuspension (MR solution) to a precipitate obtained after the centrifuging in step (b) to suspend an obtained protoplast, aspirating a suspension solution with a pipette and gently adding along the tube wall into another centrifuge tube containing an MP culture solution, conducting centrifugation, and collecting an obtained ring-band protoplast; rinsing the ring-band protoplast 2 times with an MPS wash solution; suspending and washing the ring-band protoplast one time with an E culture solution; and then resuspending the ring-band protoplast in the E culture solution and diluting to a concentration of $5\times10^4$ cells/mL to obtain a protoplast suspension.

Further, the E culture solution has a pH value of 5.6 to 6.0, and includes the following components: 1,900 mg/L of potassium nitrate, 440 mg/L of calcium chloride dihydrate, 370 mg/L of magnesium sulfate heptahydrate, 170 mg/L of potassium dihydrogen phosphate, 3.1 mg/L of boric acid, 0.42 mg/L of potassium iodide, 0.13 mg/L of sodium molybdate dihydrate, 0.013 mg/L of cobalt chloride hexahydrate, 11.16 mg/L of manganese sulfate tetrahydrate, 4.3 mg/L of zinc sulfate heptahydrate, 0.013 mg/L of copper sulfate pentahydrate, 13.94 mg/L of ferrous sulfate heptahydrate, 18.64 mg/L of disodium ethylenediaminetetraacetate (EDTA-2Na), 0.5 mg/L of vitamin B1, 0.5 mg/L of vitamin B6, 5.0 mg/L of nicotinic acid, 0.05 mg/L of biotin, 2.0 mg/L of glycine, 0.5 mg/L of folic acid, 100 mg/L of casein hydrolysate, 10 mg/L of pyruvic acid, 20 mg/L of DL-malic acid, 20 mg/L of citric acid, 500 mg/L of bovine serum albumin (BSA), 0 mg/L to 1.0 mg/L of NAA, 0.4 mg/L of 6-benzylaminopurine, 0 mg/L to 2.0 mg/L of 2,4-dichlorophenoxyacetic acid (2,4-D), 0.15 mol/L of D-mannitol, 50 mol/L of myo-inositol, 125 mol/L of xylitol, 125 mol/L of sorbitol, 125 mol/L of D-cellobiose, 125 mol/L of glucose, 0.15 mol/L of sucrose, and sterile water as a solvent.

Further, step (3) specifically includes: subjecting a protoplast suspension prepared in step (2) to static culture in the dark at 21° C. to 24° C. for 25 days to proliferate into a small cell cluster, thereby forming a callus.

Beneficial Effects: the present disclosure provides a method for high-efficiency regeneration of potato protoplast. Using potato leaves as a donor material, the method designs specialized media and culture conditions for synchronization and induction regeneration. The protocol includes: test-tube seedling cultivation, protoplast preparation, callus proliferation, callus synchronization, and callus induction regeneration. By enhancing synchronization levels in protoplast-derived callus formation and increasing bud regeneration rates, protoplasts carrying target traits more readily develop into regenerated plantlets. This method boosts plantlet regeneration efficiency, shortens the regeneration timeline, accelerates potato breeding cycles, and operates year-round and location-independently. This approach also enables high-throughput production of virus-free potato plantlets, and reduces production costs by minimizing subculture demands and preservation of foundation stocks.

BRIEF DESCRIPTION OF THE DRAWINGS

To describe the technical solutions in the embodiments of the present invention or in the prior art more clearly, the following briefly describes the accompanying drawings required for describing the embodiments or the prior art. Apparently, the accompanying drawings in the following description show merely some embodiments of the present invention, and a person of ordinary skill in the art may still derive other drawings from these accompanying drawings without creative efforts.

FIG. 13A: 0 mg/L, FIG. 13B: 1 mg/L, FIG. 13C: 3 mg/L, FIG. 13D: 5 mg/L, FIG. 13E: 7 mg/L.

DETAILED DESCRIPTION OF THE EMBODIMENTS

The technical solutions of the examples of the present disclosure are clearly and completely described below with reference to the drawings in the examples of the present disclosure. Apparently, the described examples are merely a part rather than all of the embodiments of the present disclosure. All other examples obtained by those of ordinary skill in the art based on the examples of the present disclosure without creative efforts shall fall within the protection scope of the present disclosure.

All quantitative tests in the following examples are set to run in triplicate, and the results are averaged.

Example 1: a Method for High-Efficiency Regeneration of a Potato Protoplast

Figure 1:
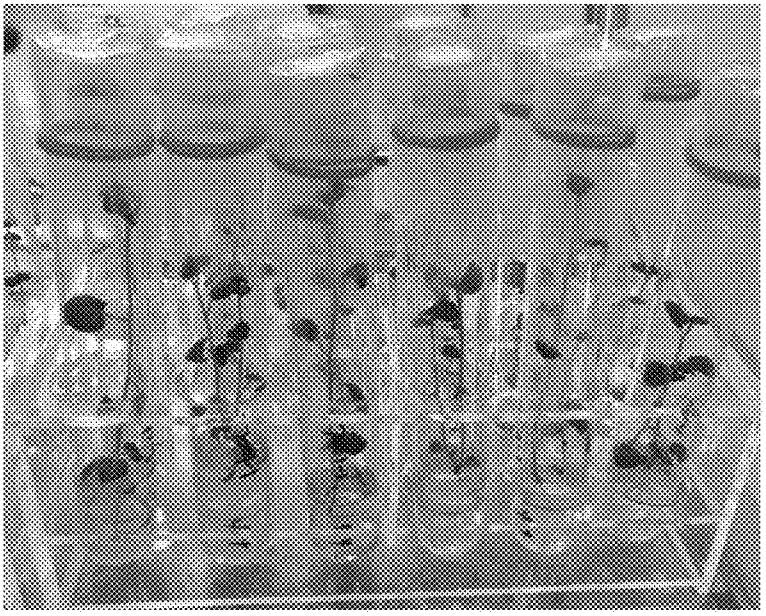
FIG. 1 shows a picture of test-tube seedling cultivation in Example 1.

A method for high-efficiency regeneration of a potato protoplast included the following step (1) to step (5):

step (1). Test-tube seedling cultivation: as shown in FIG. 1, potato tissue-cultured seedlings (Ganyin No. 9) were placed in MS medium and cultivated under alternating light/dark cycles: 16 hours under light at 23° C. and 8 hours in darkness at 20° C. for 3 weeks.

Figure 2:
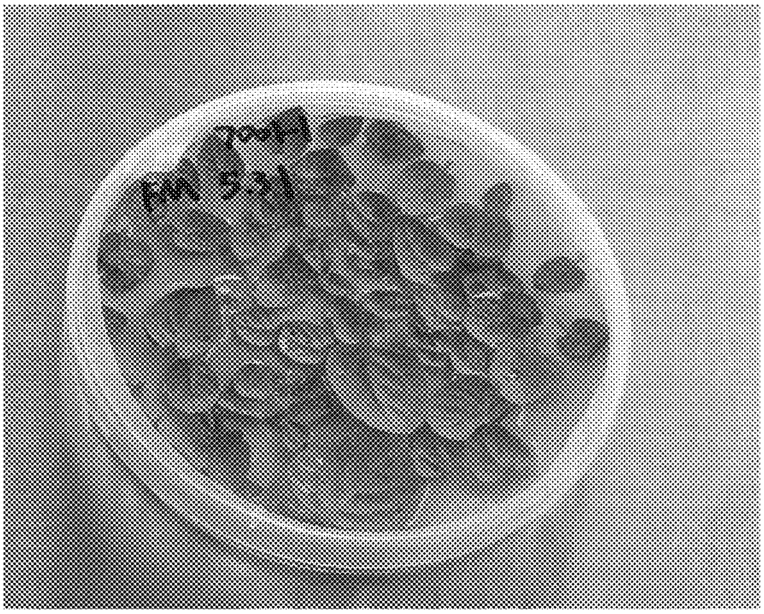
FIG. 2 shows a picture of leaf pre-cultivation in Example 1.

Step (2). Protoplast preparation (including step (a) to step (c)):

step (a). Pre-cultivation: under sterile conditions, 2-3 fully expanded leaves on the upper part of seedlings cultivated in step (1) were transferred to pre-treatment medium I. As shown in FIG. 2, dark cultivation was conducted at 24° C. for 72 hours. Pre-treatment medium I was then removed, and the treated leaves were transferred to pre-treatment medium II for incubation at 4° C. for 24 hours.

Step (b). Enzymatic digestion: pre-cultivated leaves from step (a) were cut into 0.5-1.0 mm strips, immersed in 15 mL of enzymatic digestion solution, and subjected to dark incubation at 28° C. for 9-10 hours. Post-digestion, the solution was filtered through a 240-mesh nylon sieve; the filtrate was centrifuged at 800 rpm for 8 min, and the supernatant was discarded.

Figure 3:
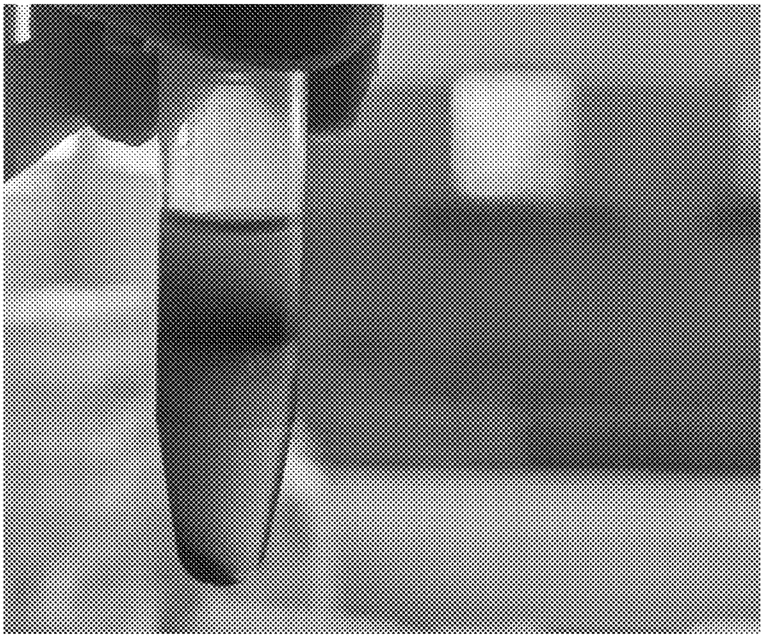
FIG. 3 shows a picture of ring-band protoplasts in Example 1.
Figure 4:
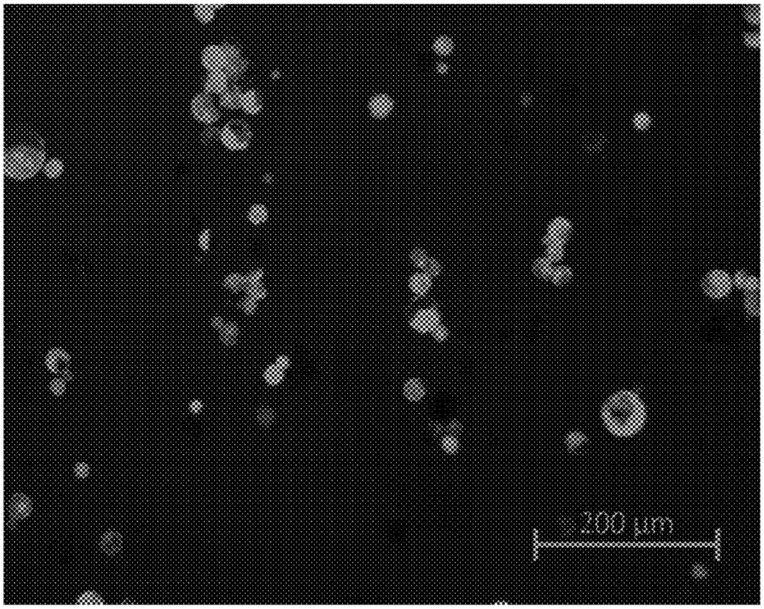
FIG. 4 shows a micrograph of the protoplast suspension in Example 1.

Step (c). Protoplast purification: 1 mL of MR solution was added to the precipitate from step (b) to suspend protoplasts. The suspension was pipetted and gently layered along the tube wall into a 5 mL centrifuge tube containing 2.5 mL of MP culture solution, followed by centrifugation at 500 rpm for 5 min. As shown in FIG. 3, ring-band protoplasts were collected. These were rinsed 2 times with an MPS wash solution, suspended/washed once with E culture solution, then resuspended in E culture solution and diluted to $5\times10^4$ cells/mL to obtain a protoplast suspension (FIG. 4).

Figure 5:
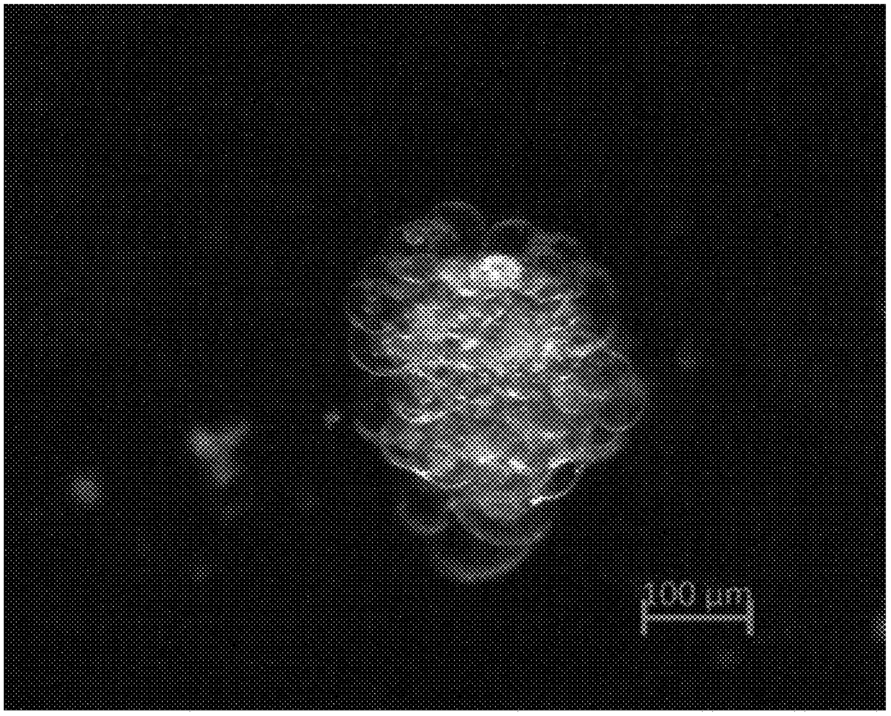
FIG. 5 shows a micrograph of proliferated cell clusters in Example 1.

Step (3). Callus proliferation: the protoplast suspension prepared in step (2) was statically cultured at 24° C. under dark conditions for 25 days, small cell clusters proliferated and formed callus (FIG. 5).

Figure 6:
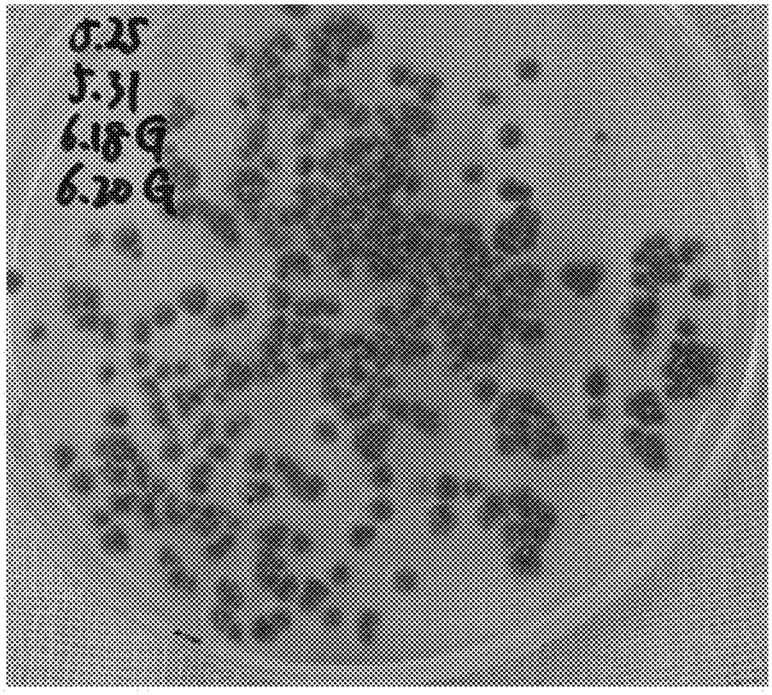
FIG. 6 shows a picture of green callus in Example 1.

Step (4). Callus synchronization treatment: callus from step (3) with diameters of 100-1,000 μm was selected, transferred to callus proliferation medium, and supplemented with synchronization proliferation medium. After incubation at 4° C. for 1 days, cultivation proceeded under alternating light/dark cycles: 16 hours under light at 23° C. and 8 hours in darkness at 20° C. for 25 days, yielding about 1.5 mm green callus (FIG. 6).

Figure 7:
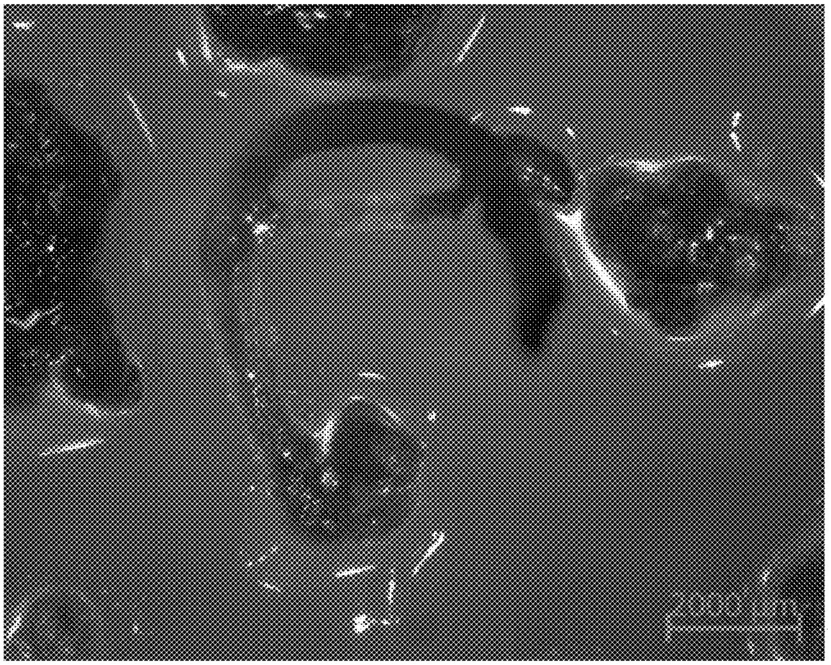
FIG. 7 shows a picture of differentiated regeneration buds in Example 1.

Step (5). Callus induction regeneration: green callus from step (4) was transferred to bud regeneration medium and cultivated under alternating light/dark cycles: 16 hours under light at 23° C. and 8 hours in darkness at 20° C. for 40 days, regeneration buds differentiated (FIG. 7).

Example 2: Reagents and Media for Potato Protoplast Regeneration

1) Pre-treatment medium I: pH from 5.6 to 6.0, included:

$NH_4NO_3$ 80 mg/L, calcium chloride dihydrate 147 mg/L, NAA 2.0 mg/L, 6-benzylaminopurine 1.0 mg/L, MES 3 mmol/L, sterile water as a solvent.

2) Pre-treatment medium II: pH from 5.6 to 6.0, included:

potassium nitrate 190 mg/L, calcium chloride dihydrate 44 mg/L, magnesium sulfate heptahydrate 37 mg/L, potassium dihydrogen phosphate 17 mg/L, boric acid 0.62 mg/L, potassium iodide 0.083 mg/L, sodium molybdate dihydrate 0.025 mg/L, cobalt chloride hexahydrate 0.0025 mg/L, manganese sulfate tetrahydrate 2.23 mg/L, zinc sulfate heptahydrate 0.86 mg/L, copper sulfate pentahydrate 0.0025 mg/L, ferrous sulfate heptahydrate 2.79 mg/L, EDTA-2Na 3.73 mg/L, vitamin B1 0.05 mg/L, vitamin B6 0.05 mg/L, nicotinic acid 0.5 mg/L, biotin 0.005 mg/L, glycine 0.2 mg/L, folic acid 0.05 mg/L, casein hydrolysate 100 mg/L, NAA 2.0 mg/L, 6-benzylaminopurine 0.5 mg/L, myo-inositol 10 mol/L, MES 3 mmol/L, sterile water as a solvent.

3) Enzymatic digestion solution: pH from 5.6 to 6.0, included: 1/10 RA solution, 0.7% cellulase R-10, 0.5% pectinase, 2% PVP, 0.2% BSA, 3 mmol/L MES, 0.4 M mannitol, sterile water to volume; where RA solution included:

potassium nitrate 1,900 mg/L, calcium chloride dihydrate 440 mg/L, magnesium sulfate heptahydrate 370 mg/L, potassium dihydrogen phosphate 170 mg/L, boric acid 3.1 mg/L, potassium iodide 0.42 mg/L, sodium molybdate dihydrate 0.13 mg/L, cobalt chloride hexahydrate 0.013 mg/L, manganese sulfate tetrahydrate 11.16 mg/L, zinc sulfate heptahydrate 4.3 mg/L, copper sulfate pentahydrate 0.013 mg/L, ferrous sulfate heptahydrate 13.94 mg/L, EDTA-2Na 18.64 mg/L, vitamin B1 0.5 mg/L, vitamin B6 0.5 mg/L, nicotinic acid 5.0 mg/L, biotin 0.05 mg/L, glycine 2.0 mg/L, folic acid 0.5 mg/L, casein hydrolysate 100 mg/L, sterile water as a solvent.

4) MR solution: pH from 5.6 to 6.0, included:

potassium nitrate 1,900 mg/L, calcium chloride dihydrate 440 mg/L, magnesium sulfate heptahydrate 370 mg/L, potassium dihydrogen phosphate 170 mg/L, boric acid 3.1 mg/L, potassium iodide 0.42 mg/L, sodium molybdate dihydrate 0.13 mg/L, cobalt chloride hexahydrate 0.013 mg/L, manganese sulfate tetrahydrate 11.16 mg/L, zinc sulfate heptahydrate 4.3 mg/L, copper sulfate pentahydrate 0.013 mg/L, ferrous sulfate heptahydrate 13.94 mg/L, EDTA-2Na 18.64 mg/L, vitamin B1 0.5 mg/L, vitamin B6 0.5 mg/L, nicotinic acid 5.0 mg/L, biotin 0.05 mg/L, glycine 2.0 mg/L, folic acid 0.5 mg/L, casein hydrolysate 100 mg/L, NAA 1.0 mg/L, 6-benzylaminopurine 0.4 mg/L, D-mannitol 0.35 mol/L, sterile water as a solvent.

5) MP culture solution: pH from 5.6 to 6.0, included:

potassium nitrate 1,900 mg/L, calcium chloride dihydrate 440 mg/L, magnesium sulfate heptahydrate 370 mg/L, potassium dihydrogen phosphate 170 mg/L, boric acid 3.1 mg/L, potassium iodide 0.42 mg/L, sodium molybdate dihydrate 0.13 mg/L, cobalt chloride hexahydrate 0.013 mg/L, manganese sulfate tetrahydrate 11.16 mg/L, zinc sulfate heptahydrate 4.3 mg/L, copper sulfate pentahydrate 0.013 mg/L, ferrous sulfate heptahydrate 13.94 mg/L, EDTA-2Na 18.64 mg/L, vitamin B1 0.5 mg/L, vitamin B6 0.5 mg/L, nicotinic acid 5.0 mg/L, biotin 0.05 mg/L, glycine 2.0 mg/L, folic acid 0.5 mg/L, casein hydrolysate 100 mg/L, NAA 1.0 mg/L, 6-benzylaminopurine 0.4 mg/L, sucrose 23% mol/L, sterile water as a solvent.

6) MPS wash solution: pH from 5.6 to 6.0, included:

potassium nitrate 1,900 mg/L, calcium chloride dihydrate 440 mg/L, magnesium sulfate heptahydrate 370 mg/L, potassium dihydrogen phosphate 170 mg/L, boric acid 3.1 mg/L, potassium iodide 0.42 mg/L, sodium molybdate dihydrate 0.13 mg/L, cobalt chloride hexahydrate 0.013 mg/L, manganese sulfate tetrahydrate 11.16 mg/L, zinc sulfate heptahydrate 4.3 mg/L, copper sulfate pentahydrate 0.013 mg/L, ferrous sulfate heptahydrate 13.94 mg/L, EDTA-2Na 18.64 mg/L, vitamin B1 0.5 mg/L, vitamin B6 0.5 mg/L, nicotinic acid 5.0 mg/L, biotin 0.05 mg/L, glycine 2.0 mg/L, folic acid 0.5 mg/L, casein hydrolysate 100 mg/L, NAA 1.0 mg/L, 6-benzylaminopurine 0.4 mg/L, D-mannitol 0.25 mol/L, myo-inositol 0.025 mol/L, sorbitol 0.025 mol/L, glucose 0.025 mol/L, sucrose 0.025 mol/L, sterile water as a solvent.

7) E culture solution: pH from 5.6 to 6.0, included:

potassium nitrate 1,900 mg/L, calcium chloride dihydrate 440 mg/L, magnesium sulfate heptahydrate 370 mg/L, potassium dihydrogen phosphate 170 mg/L, boric acid 3.1 mg/L, potassium iodide 0.42 mg/L, sodium molybdate dihydrate 0.13 mg/L, cobalt chloride hexahydrate 0.013 mg/L, manganese sulfate tetrahydrate 11.16 mg/L, zinc sulfate heptahydrate 4.3 mg/L, copper sulfate pentahydrate 0.013 mg/L, ferrous sulfate heptahydrate 13.94 mg/L, EDTA-2Na 18.64 mg/L, vitamin B1 0.5 mg/L, vitamin B6 0.5 mg/L, nicotinic acid 5.0 mg/L, biotin 0.05 mg/L, glycine 2.0 mg/L, folic acid 0.5 mg/L, casein hydrolysate 100 mg/L, pyruvic acid 10 mg/L, DL-malic acid 20 mg/L, citric acid 20 mg/L, BSA 500 mg/L, NAA 1.0 mg/L, 6-benzylaminopurine 0.4 mg/L, 2,4-D 2.0 mg/L, D-mannitol 0.15 mol/L, myo-inositol 50 mol/L, xylitol 125 mol/L, sorbitol 125 mol/L, D-cellobiose 125 mol/L, glucose 125 mol/L, sucrose 0.15 mol/L, sterile water as a solvent.

8) Callus proliferation medium: pH from 5.6 to 6.0, included:

MS medium 4.33 g/L, vitamin NN solution 1 mL/L, sucrose 30 g/L, mannitol 3 g/L, adenine sulfate 40 mg/L, myo-inositol 50 mg/L, agar 6 g/L, NAA 1 mg/L, 6-benzylaminopurine 0.5 mg/L, sterile water as a solvent.

9) Synchronization proliferation medium: pH from 5.6 to 6.0, included:

MS medium 4.33 g/L, glycine 2 mg/L, myo-inositol 150 mg/L, thiamine hydrochloride (vitamin B1) 0.5 mg/L, pyridoxine (vitamin B6) 0.5 mg/L, nicotinic acid 5 mg/L, folic acid 0.5 mg/L, biotin 0.05 mg/L, sucrose 30 g/L, mannitol 3 g/L, adenine sulfate 40 mg/L, NAA 1 mg/L, 6-benzylaminopurine 0.4-1.0 mg/L, IAA 0.5 mg/L, ABA 5 mg/L, sterile water as a solvent.

10) Bud regeneration medium: pH from 5.6 to 6.0, included:

MS medium 4.4 g/L, sucrose 10 g/L, zeatin or t-zeatin 1 mg/L, NAA 0.01 mg/L, $GA_3$ 0-0.1 mg/L, agar 6 g/L, sterile water as a solvent.

Other solutions, reagents, and media were commercially available products.

Figure 8:
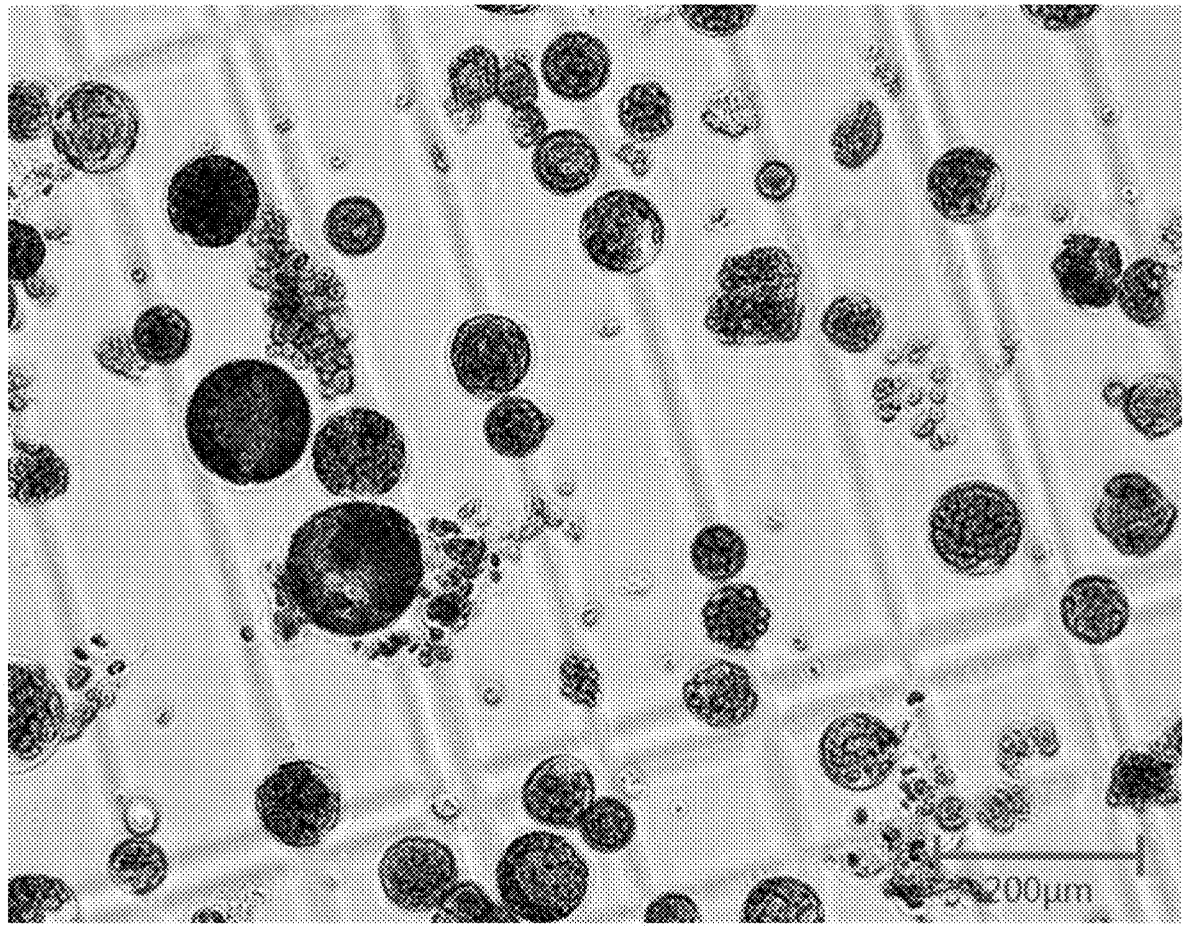
FIG. 8 shows a bright-field fluorescence micrograph of protoplasts in Example 3.
Figure 9:
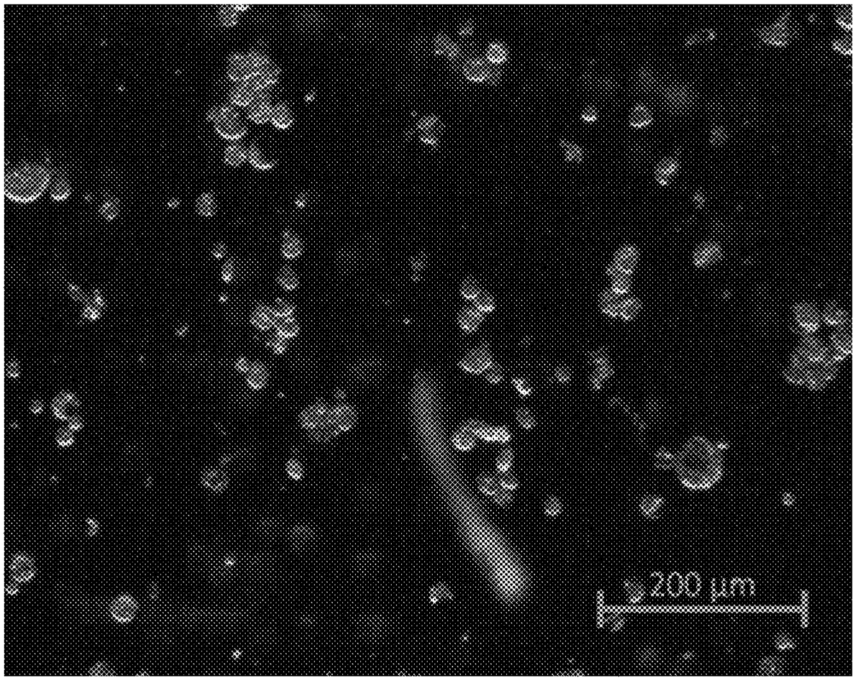
FIG. 9 shows a fluorescence micrograph of FDA-stained protoplast suspension in Example 3.

Example 3: Protoplast Viability Assay 0.1 mL of the protoplast suspension obtained in step (2) of Example 1 was mixed with 2 μL of FDA staining solution. After standing at room temperature for 5 min, protoplast viability was examined. As shown in FIG. 8 and FIG. 9, the majority of protoplast cells in the protoplast suspension from step (2) exhibited viability and were capable of further proliferation into callus for subsequent bud induction.

Example 4: Bud Induction and Regeneration Efficacy

In step (5) of Example 1, green callus from step (4) was transferred to bud regeneration medium. After 40 days of cultivation, bud emergence was quantified. Results demonstrated bud induction within 40 days, at least 25 days earlier than reported in existing technologies.

Figure 10:
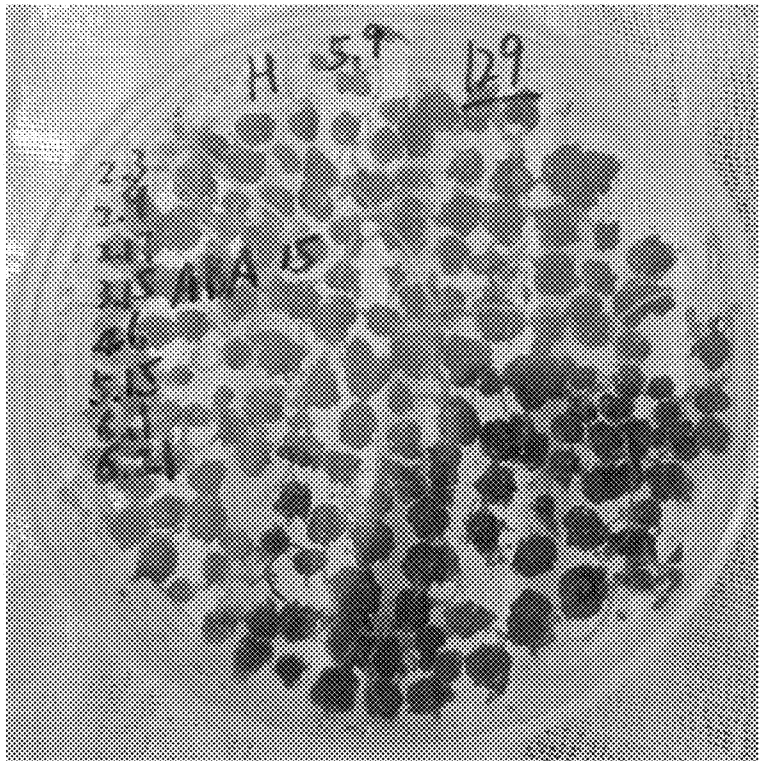
FIG. 10 shows a picture of differentiation and regeneration at 100 days in Example 4.

After the initial 40-day regeneration phase, cultivation continued for an additional 30 days and 60 days. Regeneration rates were calculated as: Regeneration rate=number of calli producing regeneration buds/500 calli*100% (based on 500 calli as a cardinal). Results showed 32.7% regeneration rate after additional 30 days; 67.9% regeneration rate after additional 60 days (100 days total; differentiation and regeneration after callus induction and regeneration culture for 40 days+continued culture for 60 days, as shown in FIG. 10).

Figure 11:
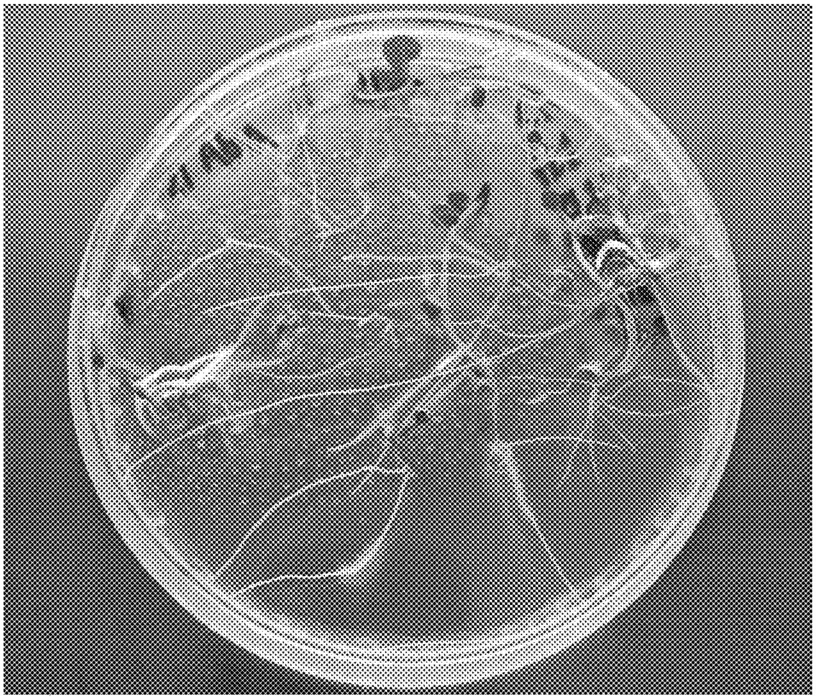
FIG. 11 shows a picture of regeneration bud propagation at 15 days in Example 4.

Regeneration buds from step (5) of Example 1 were transferred to MS medium for rooting or propagation. After 15 days, plantlets developed roots normally (FIG. 11).

Comparative Example 1: Component Screening for Synchronization Proliferation Medium A synchronization proliferation medium (pH=5.6-6.0) included: MS medium 4.33 g/L, glycine 2 mg/L, myo-inositol 150 mg/L, thiamine hydrochloride (vitamin B1) 0.5 mg/L, pyridoxine (vitamin B6) 0.5 mg/L, nicotinic acid 5 mg/L, folic acid 0.5 mg/L, biotin 0.05 mg/L, sucrose 30 g/L, mannitol 3 g/L, adenine sulfate 40 mg/L, NAA 1 mg/L, 6-benzylaminopurine 0.4-1.0 mg/L, IAA 0.5 mg/L, sterile water as a solvent, with ABA supplementation.

This experiment screened optimal ABA concentrations for synchronization efficacy of synchronization proliferation medium.

Five ABA concentration gradients were tested: 0 mg/L, 1 mg/L, 3 mg/L, 5 mg/L, and 7 mg/L, while other components and concentrations of the synchronization proliferation medium remained unchanged, and the method for high-efficiency regeneration of a potato protoplast was the same as that in Example 1, in order to screen out an ABA concentration that was beneficial to improving the synchronization level.

Figure 12:
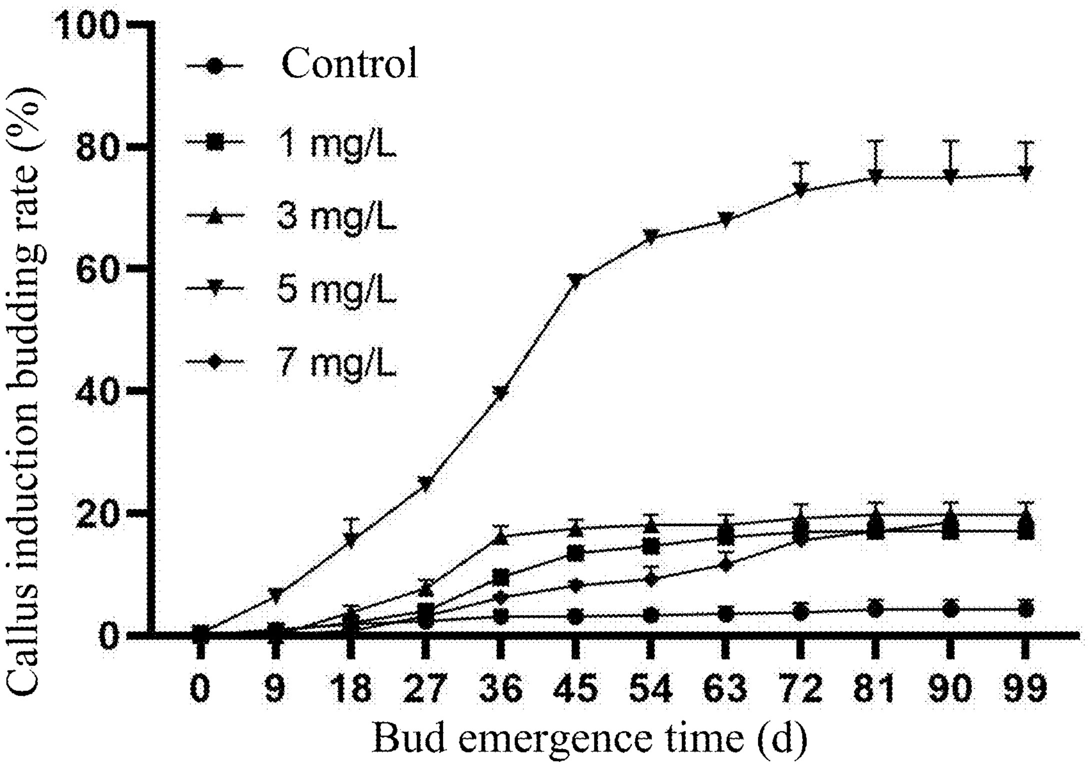
FIG. 12 shows the effect of synchronization proliferation medium samples with different ABA concentrations on callus induction budding rate in Comparative Example 1.
Figure 13A:
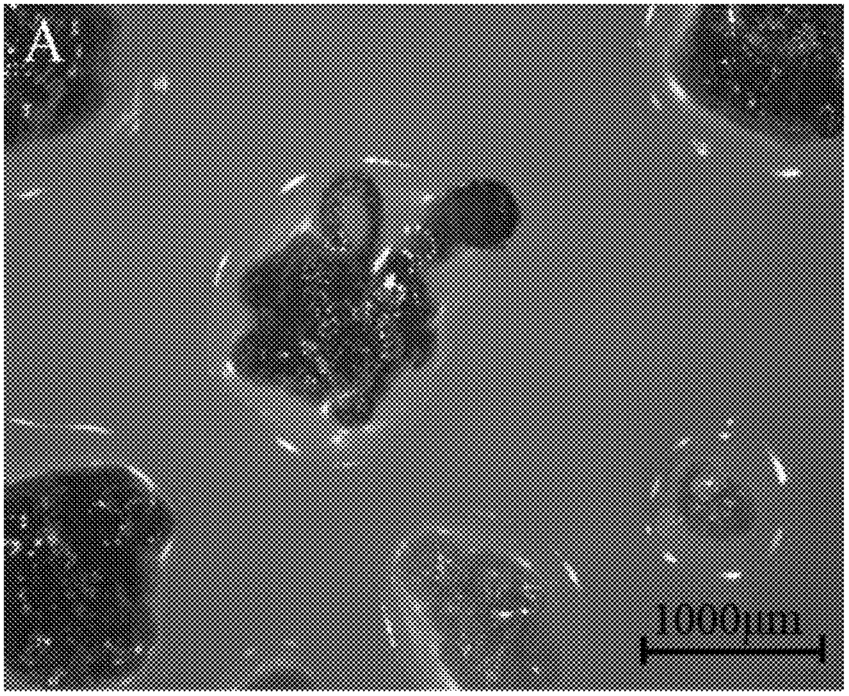
FIGS. 13A-13E show callus induction bud regeneration phenotypes under synchronization proliferation medium samples with different ABA concentrations in Comparative Example 1; where letters indicate
Figure 13B:
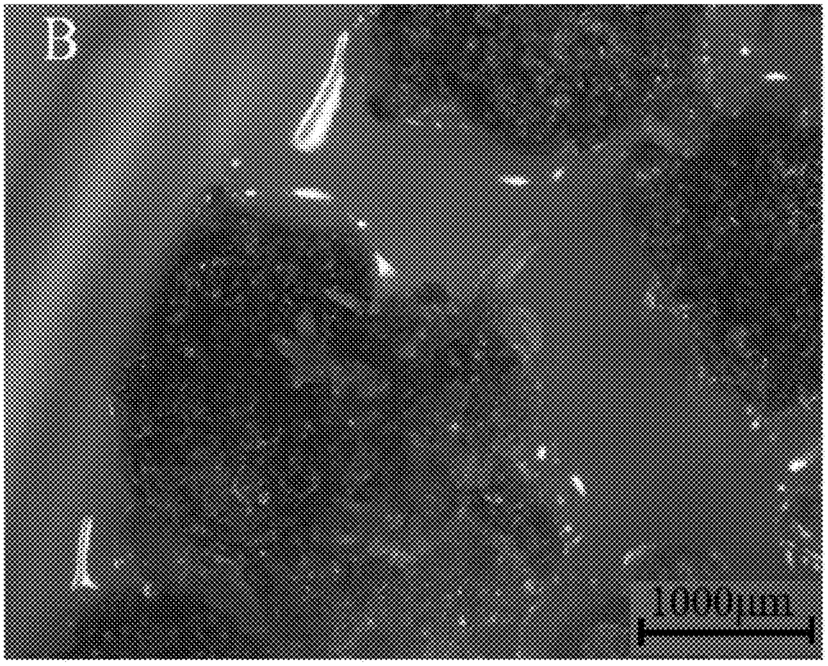
Figure 13C:
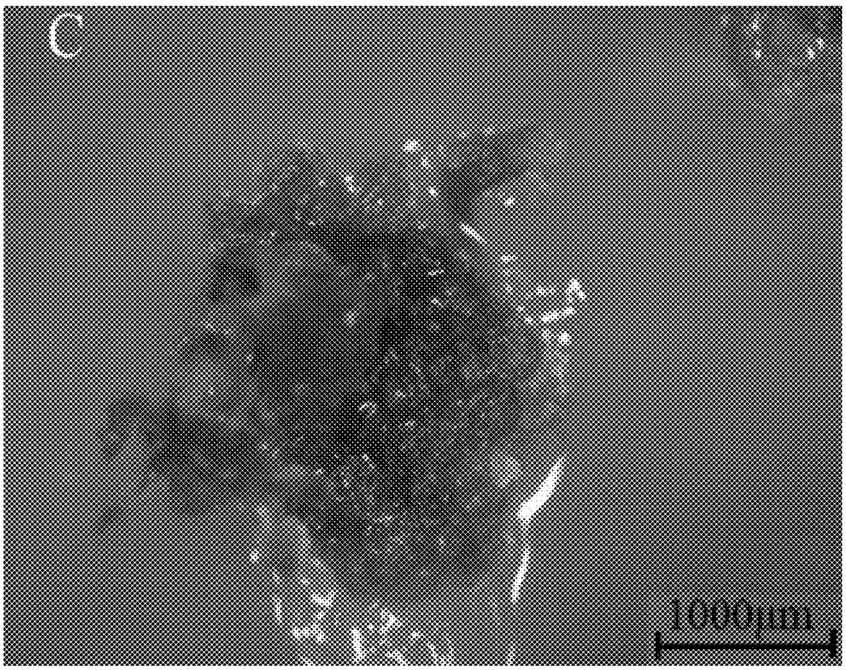
Figure 13D:
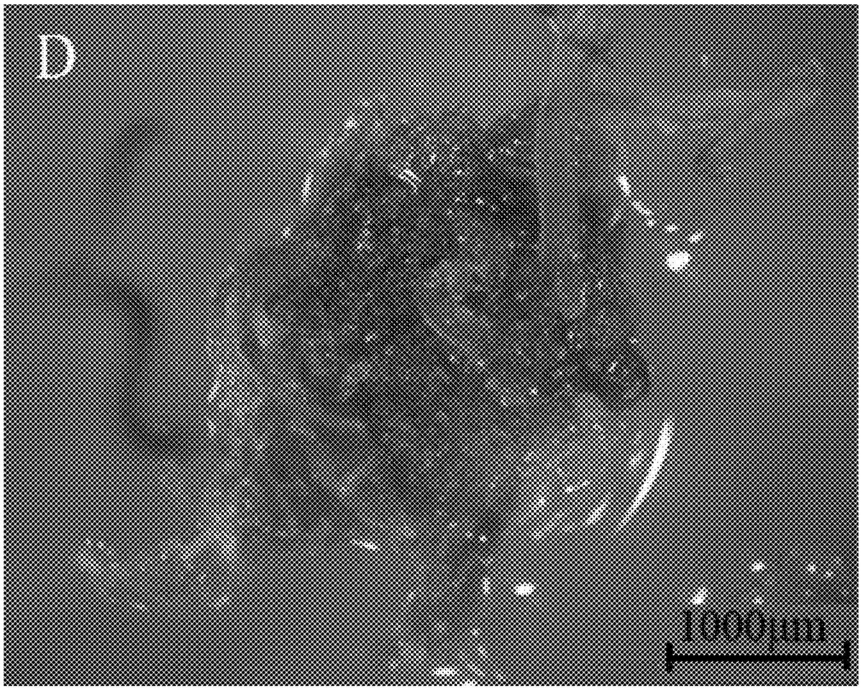
Figure 13E:
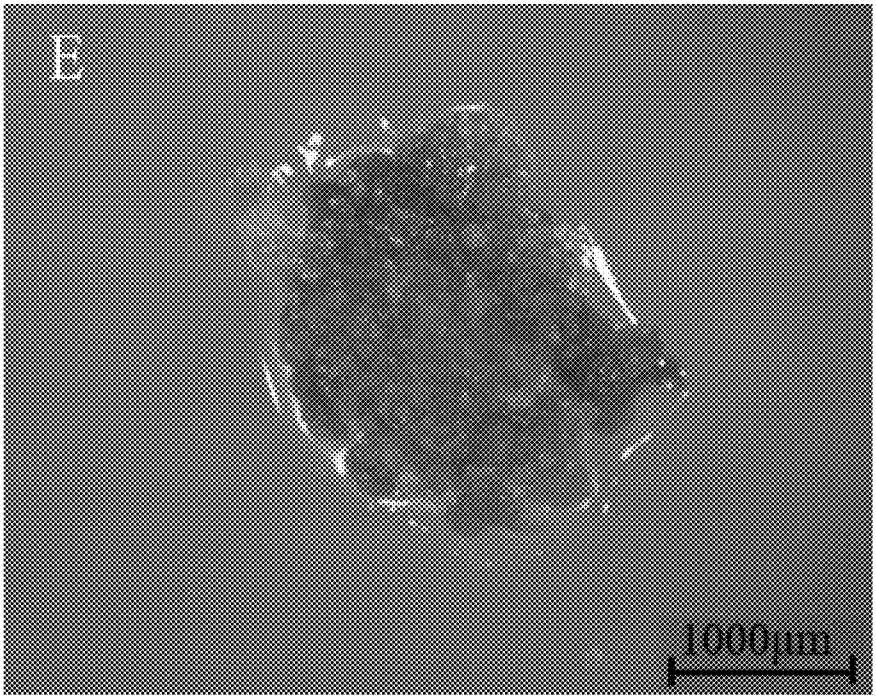

Results demonstrated (FIG. 12): all ABA concentrations (0-7 mg/L) induced budding from callus; 5 mg/L ABA significantly elevated bud induction rates versus other concentrations; enhanced synchronization was achieved at same concentration, accelerating callus proliferation and increasing overall yield.

Additionally, phenotypic comparison (FIGS. 13A-13E) confirmed superior bud regeneration capacity of callus at 5 mg/L ABA.

Comparative Example 2: Comparative Analysis with Existing Technologies

The experimental group (Method of Example 1) was compared with: Control Group (1) (Prior art: LI, Xiao. Study on Potato Protoplast Culture, Regeneration, and Transient CRISPR/Cas9 Transformation; medium: MS medium+1 mg/L ZT+0.01 mg/L NAA+0.01 mg/L $GA_3$+1 mg/L KT+2% sucrose); Control Group (2) (Prior art: CAI, Xingkui. Creation of Bacterial Wilt-Resistant Potato Germplasm via Protoplast Fusion and Genetic Analysis; medium: 0.5 mg/L IAA+2.5 mg/L zeatin). Results were summarized in Table 1.

TABLE 1

Comparison of callus induction regeneration timelines and rates for leaf-derived protoplasts

| Technique indexes | (1) | (2) | Experimental group | Remarks |
|---|---|---|---|---|
| Cultivation time of test-tube seedling | 21 d | 21 d | 21 d | / |
| Preparation time of protoplast | 5 d | 4 d | 5 d | / |
| Proliferation time of callus | 60 d | 63 d | 25 d | / |
| Synchronization time of callus | / | / | 25 d | / |
| Time of induction regeneration (appearance time of the first regeneration bud) | 55 d | 60 d | 40 d | / |
| Regeneration rate (on day 60 after the first regeneration bud appeared) | 22.9% | 16.7% | ≥67.9% | There was no data on the time of regeneration budding in (1) and (2) |

Results showed that existing technologies lacked the use of synchronization; the present method for high-efficiency regeneration of a potato protoplast provided significantly reduced the regeneration cycle from a cell to a plant. From callus proliferation to budding through callus induction regeneration, it took about 4 months (callus proliferation to bud induction) in the prior art, while it took 3 months in the present disclosure. Prior art provides about 20% regeneration rate (requiring ≥6 months), while the present disclosure exhibited >60% regeneration rate within 5 months. The present method could achieve the highest regeneration rate within the shortest timeframe, offering distinct advantages for research and commercial applications.

The above described are merely preferred embodiments of the present disclosure, and not intended to limit the present disclosure. Any modifications, equivalent replacements and improvements made within the spirit and principle of the present disclosure should all fall within the scope of protection of the present disclosure.

What is claimed is:

1. A method for high-efficiency regeneration of a potato protoplast, comprising the following steps:

step (1) conducting test-tube seedling cultivation;

step (2) conducting protoplast preparation; wherein step (2) comprises:

step (a) conducting pre-cultivation: taking 2 to 3 fully expanded leaves on an upper part of a potato test-tube seedling cultivated in step (1) under sterile conditions, placing the leaves into pre-treatment medium I to allow cultivation in the dark at 24° C. for 1 days to 5 days, removing the pre-treatment medium I, and then transferring the leaves cultivated in the pre-treatment medium I into pre-treatment medium II to allow incubation in a refrigerator at 4° C. for 24 hours;

step (b) conducting enzymatic digestion: cutting pre-cultivated leaves obtained from step (a) into thin strips, immersing the thin strips in an enzymatic digestion solution to allow incubation in the dark at 28° C. for 9 hours to 10 hours, filtering an obtained enzymatic hydrolysate, centrifuging an obtained filtrate, and then discarding an obtained supernatant; and step (c) conducting protoplast purification: adding a Medium for Resuspension (MR solution) to a precipitate obtained after the centrifuging in step (b) to suspend an obtained protoplast, transferring an obtained suspension to an MP culture solution, conducting centrifugation, and collecting an obtained ring-band protoplast; rinsing the ring-band protoplast 2 times with an MPS wash solution; suspending and washing the ring-band protoplast one time with an E culture solution; and then resuspending the ring-band protoplast in the E culture solution and diluting to a concentration of $5\times10^4$ cells/mL to obtain a protoplast suspension;

step (3): conducting callus proliferation, comprising: subjecting the protoplast suspension prepared in step (2) to static culture in the dark at 21° C. to 24° C. for 25 days to proliferate into a small cell cluster, thereby forming a callus;

step (4): conducting callus synchronization: selecting a callus fragment with a diameter of 100 μm to 1,000 μm from the callus obtained in step (3), transferring the callus fragment to a callus proliferation medium, adding a synchronization proliferation medium to allow cultivation at 4° C. to 7° C. for 1 day to 3 days, and then conducting cultivation for 25 days in a cycle under light conditions at 20° C. to 23° C. for 16 hours and in the dark at 18° C. to 20° C. for 8 hours to form a green callus; and step (5); conducting callus induction regeneration: transferring the green callus obtained in step (4) to a bud regeneration medium to allow cultivation for 40 days in cycles under light conditions at 20° C. to 23° C. for 16 hours and in the dark at 18° C. to 20° C. for 8 hours to differentiate a regeneration bud; wherein the pre-treatment medium I has a pH value of 5.6 to 6.0 and consists of 80 mg/L of $NH_4NO_3$, 147 mg/L of calcium chloride dihydrate, 2.0 mg/L of naphthaleneacetic acid (NAA), 1.0 mg/L of 6-benzylaminopurine, 3 mmol/L of 2-(N-morpholino) ethanesulfonic acid (MES), and sterile water;

the pre-treatment medium II has a pH value of 5.6 to 6.0 and consists of 190 mg/L of potassium nitrate, 44 mg/L of calcium chloride dihydrate, 37 mg/L of magnesium sulfate heptahydrate, 17 mg/L of potassium dihydrogen phosphate, 0.62 mg/L of boric acid, 0.083 mg/L of potassium iodide, 0.025 mg/L of sodium molybdate dihydrate, 0.0025 mg/L of cobalt chloride hexahydrate, 2.23 mg/L of manganese sulfate tetrahydrate, 0.86 mg/L of zinc sulfate heptahydrate, 0.0025 mg/L of copper sulfate pentahydrate, 2.79 mg/L of ferrous sulfate heptahydrate, 3.73 mg/L of disodium ethylenediaminetetraacetate (EDTA-2Na), 0.05 mg/L of vitamin B1, 0.05 mg/L of vitamin B6, 0.5 mg/L of nicotinic acid, 0.005 mg/L of biotin, 0.2 mg/L of glycine, 0.05 mg/L of folic acid, 100 mg/L of casein hydrolysate, 2.0 mg/L of NAA, 0.5 mg/L of 6-benzylaminopurine, 10 mol/L of myo-inositol, 3 mmol/L of MES, and sterile water;

the MR solution has a pH value of 5.6 to 6.0 and consists of 1,900 mg/L of potassium nitrate, 440 mg/L of calcium chloride dihydrate, 370 mg/L of magnesium sulfate heptahydrate, 170 mg/L of potassium dihydrogen phosphate, 3.1 mg/L of boric acid, 0.42 mg/L of potassium iodide, 0.13 mg/L of sodium molybdate dihydrate, 0.013 mg/L of cobalt chloride hexahydrate, 11.16 mg/L of manganese sulfate tetrahydrate, 4.3 mg/L of zinc sulfate heptahydrate, 0.013 mg/L of copper sulfate pentahydrate, 13.94 mg/L of ferrous sulfate heptahydrate, 18.64 mg/L of EDTA-2Na, 0.5 mg/L of vitamin B1, 0.5 mg/L of vitamin B6, 5.0 mg/L of nicotinic acid, 0.05 mg/L of biotin, 2.0 mg/L of glycine, 0.5 mg/L of folic acid, 100 mg/L of casein hydrolysate, 1.0 mg/L of NAA, 0.4 mg/L of 6-benzylaminopurine, 0.35 mol/L of D-mannitol, and sterile water;

the MP culture solution has a pH value of 5.6 to 6.0 and consists of 1,900 mg/L of potassium nitrate, 440 mg/L of calcium chloride dihydrate, 370 mg/L of magnesium sulfate heptahydrate, 170 mg/L of potassium dihydrogen phosphate, 3.1 mg/L of boric acid, 0.42 mg/L of potassium iodide, 0.13 mg/L of sodium molybdate dihydrate, 0.013 mg/L of cobalt chloride hexahydrate, 11.16 mg/L of manganese sulfate tetrahydrate, 4.3 mg/L of zinc sulfate heptahydrate, 0.013 mg/L of copper sulfate pentahydrate, 13.94 mg/L of ferrous sulfate heptahydrate, 18.64 mg/L of EDTA-2Na, 0.5 mg/L of vitamin B1, 0.5 mg/L of vitamin B6, 5.0 mg/L of nicotinic acid, 0.05 mg/L of biotin, 2.0 mg/L of glycine, 0.5 mg/L of folic acid, 100 mg/L of casein hydrolysate, 1.0 mg/L of NAA, 0.4 mg/L of 6-benzylaminopurine, 0.23 mol/L of sucrose, and sterile water;

the MPS wash solution has a pH from 5.6 to 6.0 and consists of the following components: potassium nitrate 1,900 mg/L, calcium chloride dihydrate 440 mg/L, magnesium sulfate heptahydrate 370 mg/L, potassium dihydrogen phosphate 170 mg/L, boric acid 3.1 mg/L, potassium iodide 0.42 mg/L, sodium molybdate dihydrate 0.13 mg/L, cobalt chloride hexahydrate 0.013 mg/L, manganese sulfate tetrahydrate 11.16 mg/L, zinc sulfate heptahydrate 4.3 mg/L, copper sulfate pentahydrate 0.013 mg/L, ferrous sulfate heptahydrate 13.94 mg/L, EDTA-2Na 18.64 mg/L, vitamin B1 0.5 mg/L, vitamin B6 0.5 mg/L, nicotinic acid 5.0 mg/L, biotin 0.05 mg/L, glycine 2.0 mg/L, folic acid 0.5 mg/L, casein hydrolysate 100 mg/L, NAA 1.0 mg/L, 6-benzylaminopurine 0.4 mg/L, D-mannitol 0.25 mol/L, myo-inositol 0.025 mol/L, sorbitol 0.025 mol/L, glucose 0.025 mol/L, sucrose 0.025 mol/L, sterile water as a solvent the E culture solution has a pH value of 5.6 to 6.0 and consists of 1,900 mg/L of potassium nitrate, 440 mg/L of calcium chloride dihydrate, 370 mg/L of magnesium sulfate heptahydrate, 170 mg/L of potassium dihydrogen phosphate, 3.1 mg/L of boric acid, 0.42 mg/L of potassium iodide, 0.13 mg/L of sodium molybdate dihydrate, 0.013 mg/L of cobalt chloride hexahydrate, 11.16 mg/L of manganese sulfate tetrahydrate, 4.3 mg/L of zinc sulfate heptahydrate, 0.013 mg/L of copper sulfate pentahydrate, 13.94 mg/L of ferrous sulfate heptahydrate, 18.64 mg/L of EDTA-2Na, 0.5 mg/L of vitamin B1, 0.5 mg/L of vitamin B6, 5.0 mg/L of nicotinic acid, 0.05 mg/L of biotin, 2.0 mg/L of glycine, 0.5 mg/L of folic acid, 100 mg/L of casein hydrolysate, 10 mg/L of pyruvic acid, 20 mg/L of DL-malic acid, 20 mg/L of citric acid, 500 mg/L of bovine serum albumin (BSA), 0 to 1.0 mg/L of NAA, 0.4 mg/L of 6-benzylaminopurine, 0 to 2.0 mg/L of 2,4-dichlorophenoxyacetic acid (2,4-D), 0.15 mol/L of D-mannitol, 50 mol/L of myo-inositol, 125 mol/L of xylitol, 125 mol/L of sorbitol, 125 mol/L of D-cellobiose, 125 mol/L of glucose, 0.15 mol/L of sucrose, and sterile water;

the callus proliferation medium has a pH value of 5.6 to 6.0 and consists of 4.33 g/L of Murashige and Skoog (MS) medium, 1 mL/L of a vitamin NN solution, 30 g/L of sucrose, 3 g/L of mannitol, 40 mg/L of adenine sulfate, 50 mg/L of myo-inositol, 6 g/L of agar, 1 mg/L of NAA, 0.5 mg/L of 6-benzylaminopurine, and sterile water;

the synchronization proliferation medium has a pH value of 5.6 to 6.0 and consists of 4.33 g/L of MS medium, 2 mg/L of glycine, 150 mg/L of myo-inositol, 0.5 mg/L of thiamine hydrochloride (vitamin B1), 0.5 mg/L of pyridoxine (vitamin B6), 5 mg/L of nicotinic acid, 0.5 mg/L of folic acid, 0.05 mg/L of biotin, 30 g/L of sucrose, 3 g/L of mannitol, 40 mg/L of adenine sulfate, 1 mg/L of NAA, 0.4 to 1.0 mg/L of 6-benzylaminopurine, 0.5 mg/L of indole-3-acetic acid (IAA), 0 mg/L to 5 mg/L of abscisic acid (ABA), and sterile water; and the bud regeneration medium has a pH value of 5.6 to 6.0 and consists of 4.4 g/L of MS medium, 10 g/L of sucrose, 1 mg/L of zeatin or t-zeatin, 0.01 mg/L of NAA, 0 to 0.1 mg/L of gibberellic acid ($GA_3$), 6 g/L of agar, and sterile water.

2. The method for high-efficiency regeneration of the potato protoplast according to claim 1, wherein step (1) comprises: subjecting a potato test-tube seedling to cultivation for 3 to 4 weeks in cycles under light conditions at 20° C. to 23° C. for 16 hours and in the dark at 18° C. to 20° C. for 8 hours.

* * * * *